United States Patent [19]

Segawa et al.

[11] Patent Number: 4,906,747

[45] Date of Patent: Mar. 6, 1990

[54] PROCESS FOR PRODUCING A METAL PHTHALOCYANINE AND/OR ITS DERIVATIVE

[75] Inventors: Tomio Segawa; Kazuhiro Maruyama; Tadashi Ninomiya; Motokazu Suyama, all of Kawasaki, Japan

[73] Assignee: Kawasaki Kasei Chemicals Ltd., Tokyo, Japan

[21] Appl. No.: 284,613

[22] Filed: Dec. 15, 1988

[30] Foreign Application Priority Data

Dec. 31, 1987 [JP] Japan .................. 62-336849

[51] Int. Cl.$^4$ .................. C07D 251/32; C09B 19/00
[52] U.S. Cl. .................. 540/144; 544/192
[58] Field of Search .................. 540/144; 544/192

[56] References Cited

U.S. PATENT DOCUMENTS 4,109,089  8/1978  Cooker et al. .................. 544/192

FOREIGN PATENT DOCUMENTS 573859  1/1982  Japan .
57-25361  2/1982  Japan .
57-135866  8/1982  Japan .
57-170961  10/1982  Japan .

OTHER PUBLICATIONS

Kawasaki Kasei Chemicals, Chem. Abstracts, vol. 98, 1983, 108878e.

*Primary Examiner*—Mukund J. Shah
*Assistant Examiner*—Edward C. Ward
*Attorney, Agent, or Firm*—Oblon, Spivak, McClelland, Maier & Neustadt

[57] ABSTRACT

In a process for producing a metal phthalocyanine and/or its derivative by heating phthalic anhydride and/or its derivative, urea and a metal compound in an organic solvent in the presence of a catalyst, or by heating phthalodinitrile and a metal or a metal compound in an organic solvent, the improvement wherein the reaction for the production of the metal phthalocyanine and/or its derivative is conducted by an addition of cyanuric acid and/or its derivative.

3 Claims, No Drawings

PROCESS FOR PRODUCING A METAL PHTHALOCYANINE AND/OR ITS DERIVATIVE

BACKGROUND OF THE INVENTION

1. Field of the Invention

The present invention relates to an industrially advantageous novel process for producing a metal phthalocyanine and/or its derivative (hereinafter sometimes referred to simply as metal phthalocyanines).

2. Discussion of Background

Metal phthalocyanines are pigments which are most important from the industrial point of view. Among them, copper phthalocyanines have beautiful blue colors and excellent properties such as heat resistance, chemical resistance and light resistance, and they are widely used in the field of coating materials, printing inks or resin coloring agents, mainly as blue pigments. In the following description, such copper phthalocyanines will be used as typical example for detailed description.

A number of methods have been proposed for the preparation of copper phthalocyanines. Among them, a so-called phthalodinitrile method and a phthalic anhydride-urea method (hereinafter referred to simply as a urea method) are industrially important. It is common to employ the urea method for the preparation of copper phthalocyanines in a large amount on an industrial scale.

The urea method is a method wherein phthalic anhydride, phthalic acid or its derivative and urea, a copper compound and a catalyst are heated in the presence of an organic solvent. As the derivative of phthalic acid, an ammonium salt of phthalic acid, phthalimide, a phthalic acid ester, a phthalic acid amide or orthocyanobenzoic acid may be mentioned. Such phthalic anhydride, phthalic acid or its derivatives may be used alone or in combination as a mixture of two or more.

As the nitrogen source for copper phthalocyanines, ammonia and biuret are known in addition to urea. However, industrially, urea is mainly used. In literatures such as patents, cyanuric acid is usually disclosed as this nitrogen source. However, there has been no instance wherein a metal phthalocyanine is prepared by using cyanuric acid. In fact, according to the experiments by the present inventors, cyanuric acid does not function as the nitrogen source in the reaction of this type.

As the copper compound, copper halide such as cuprous chloride is most commonly used industrially. However, a metal copper, copper oxide, copper cyanide, copper sulfate, copper nitrate and copper acetate may also be employed for this purpose. The amount of the copper compound is most advantageously at a level of 1 mol per 4 mol of phthalic anhydride from the viewpoint of yield. Use of the copper compound in an excess amount not only brings about a reduction in the yield but also is industrially disadvantageous from the viewpoint of environmental pollution due to an increase of copper ions discharged into a waste water from the purification.

As the catalyst, a molybdenum compound such as ammonium molybdate, molybdic acid, phosphorus molybdic acid, ammonium phosphorus molybdate or molybdenum oxide. Among them, ammonium molybdate is particularly superior. In addition to the above, arsenic vanadium compound, boric acid or a halide or an oxyhalide of titanium, tin or antimony, may be used.

As the solvent for the reaction of the urea method, an inexpensive organic solvent which is thermally stable and not reactive with the reaction product during the reaction and which is liquid at room temperature and has a narrow range of the boiling point within a range of from 170° to 240° C. and low toxicity is suitable for industrial purpose. Heretofore, trichlorobenzene or nitrobenzene has been used for an industrial operation as a solvent which substantially satisfies such conditions. However, these solvents are disfavored because of the toxicity and possible environmental polution, and recently, alkylbenzenes are favorably employed for industrial purpose.

The mechanism for the formation of copper phthalocyanines in such a urea method has not yet been completely understood. However, there are the following problems from the viewpoint of phenomena observed during the reaction for the formation of phthalocyanine.

Phthalic anhydride used as one of the main starting materials for the synthesis of copper phthalocyanine, can readily be converted to phthalimide by contacting it with ammonia gas at a temperature of at least 170° C. Therefore, it has been industrially common to convert phthalic anhydride to the imide with ammonia gas preliminarily generated by the reaction, to save the consumption of urea. Accordingly, in the reaction for the formation of copper phthalocyanine by the urea method, even if phthalic anhydride is used, the starting substance is believed to be phthalimide. At the initial stage of the reaction for the formation of copper phthalocyanine, when the reaction system is heated to a temperature of at least the melting point of urea, firstly the copper compound (mainly cuprous chloride) and the catalyst molybdenum compound are dissolved in molten urea, and this urea-cuprous chloride-molybdenum compound melt is reacted with phthalimide to form yellowish brown intermediate I. As the heating is continued at a temperature of at least 170° C., it turns into reddish brown intermediate II. As the heating is further continued, formation of copper phthalocyanine III starts to take place.

Thus, the phthalocyanine-forming reaction contains the above-mentioned three steps as the phenomena. Phthalimide has fairly good solubility in an organic solvent at a temperature of at least 170° C. when used alone. However, when it is present together with a melt of urea-cuprous chloride-molybdenum compound, phthalimide transfers from the organic solvent phase to the molten phase of the urea-cuprous chloride-molybdenum compound and reacts to form copper phthalocyanine through the above-mentioned three steps. Thus, the copper phthalocyanine-forming reaction proceeds in urea, i.e. proceeds in a phase different from the organic solvent. At the initial stage of the reaction, urea is present in an adequate amount in the liquid state and thus serves as a solvent, whereby the reaction proceeds in the urea solvent. However, as the reaction progresses, urea is consumed by the reaction, and its amount decreases as time passes and finally it will not function as the solvent. The organic solvent provides no substantial solubility to the reaction product. Therefore, when urea is consumed by the reaction and is no longer substantially present as liquid, the reaction product will be present in the form of solid in a different phase in the organic solvent. In this state, copper phthalocyanine is formed via the above-mentioned three steps. When urea has been consumed by the reaction and no longer functions as a solvent, the fluidity of the reaction product becomes poor, the reaction solution becomes rapidly viscous and the torque exerted to stirring vanes rapidly increases. In spite of forcible stirring with a clearance with the inner wall of the reaction tube set to be as small as possible by means of anchor-type stirring vanes, the moving (rotational) speed of the reaction product in contact with the inner wall of the reaction tube drops to a level of not higher than 1/100 of the rotational speed of the stirring vanes, and the reaction product does not substantially move.

The degree of the torque during the stirring of this reaction solution varies depending upon the organic solvent used. When three solvents of nitrobenzene, trichlorobenzene and an alkylbenzene which are most commonly used as organic solvents for the reaction for the synthesis of copper phthalocyanine are compared, the degree of the increase of the torque is in the order of the alkylbenzene>>trichlorobenzene>nitrobenzene. Thus, the torque is greatest in the case of the alkylbenzene which is most widely used on an industrial scale as a solvent which is safe and harmless from the viewpoint of food hygiene and environmental hygiene.

The decrease of the fluidity during the reaction for this reaction product can be compensated by an addition of an organic solvent. However, the addition of the solvent tends to lead to a decrease in the productivity due to a decrease of the space time yield, and the yield relative to the starting materials tends to decrease. Such should be avoided as far as possible.

The decrease of the fluidity and the decrease of the reaction yield by dilution with a solvent become fatal drawbacks in a case where the reaction for the synthesis of copper phthalocyanine is continuously conducted by a multi tank reaction system, since the transfer of the reaction solution between the tanks at a constant rate can not be expected at all.

Such a high viscosity phenomenon of the reaction solution due to a substantial decrease in the fluidity of the reaction product during the reaction for the synthesis of copper phthalocyanine is believed to cause non-uniformity in the reaction temperature distribution in the reaction product, since the reaction for the formation of copper phthalocyanine in the urea method is an endothermic reaction of about 80 kcal/mol and the activation energy is fairly large at a level of about 40 kcal/mol. It is believed that this brings about non-uniformity in the partial reaction rate in the reaction product, prevents the reproducibility of the reaction and causes the decrease in the reaction yield and a deterioration in the quality of the pigment as a final product.

Thus, the low fluidity due to the high viscosity of the reaction solution as time passes during the production of copper phthalocyanine by the urea method, brings about a decrease in the yield of the product (crude pigment which may be called non-pigmented crude or simply crude) and a deterioration in the quality of the pigment obtained. Further, it presents a fatal defect in the continuous operation of the reaction for the synthesis of copper phthalocyanine.

As a method for solving the problem of the conventional urea method as described above, there has been recently proposed a method wherein a large amount of solvent is used for the reaction and at the same time the agitation is enhanced, or a method wherein a surface active agent is added to the reaction mixture, for example, in Japanese Unexamined Patent Publication Nos. 10659/1987 and 10660/1987. However, the former method has a problem that it is industrially disadvantageous since the space time yield decreases, and the latter method has a problem that the surface active agent added at the time of the reaction is included dee in the formed copper phthalocyanine crystals, so that it is difficult to completely remove such surface active agent even in the subsequent purification step, and such a surface active agent is likely to substantially deteriorate the performance of a printing ink prepared by using such copper phthalocyanine.

It is an object of the present invention to solve all such conventional problems as described above and to provide novel process whereby crude metal phthalocyanines of high purity with high performance can be prepared in good yield industrially advantageously, either by the so-called urea method or the phthalodinitrile method.

SUMMARY OF THE INVENTION

The present inventors have conducted a study to accomplish such an object and as a result, have found for the first time that by the presence of cyanuric acid and/or a cyanuric acid derivative in the reaction mixture, the fluidity of the reaction product during the reaction can be remarkably improved and at the same time, the reaction yield can be improved. The present invention has been made on the basis of this discovery. Namely, the present invention provides a process for producing a metal phthalocyanine and/or its derivative by heating phthalic anhydride and/or its derivative, urea and a metal compound in an organic solvent in the presence of the catalyst, or by heating phthalodinitrile and a metal or a metal compound in an organic solvent, wherein the reaction for the production of the metal phthalocyanine and/or its derivative is conducted by an addition of cyanuric acid and/or its deriative.

DETAILED DESCRIPTION OF THE PREFERRED EMBODIMENTS

As the starting materials to be used in the urea method of the present invention, basically, materials commonly employed in the conventional urea method can be employed. Phthalic anhydride and/or phthalimide is used as the starting material particularly suitable for the present invention, and urea is used as a nitrogen source. In the case where phthalic anhydride is used as the starting material, the highest yield can be obtained when at least 3 mols of urea is used per mol of phthalic acid. Since urea undergoes decomposition during the reaction, it is usual to employ an excess amount at a level of from 3.5 to 4.0 mols of urea. In the case where phthalimide is used as the phthalic acid starting material, copper phthalocyanine is produced in the best yield when at least 2 mols of urea is used per mol of phthalimide. However, it is usual to employ from 2.2 to 3.0 mols of urea taking the thermal decomposition of urea into accounts.

As the copper compound, it is preferred to employ cuprous chloride. It is most advantageous to use it in an amount of about 1 mol relative to 4 mols of phthalic anhydride or phthalimide from the viewpoint of the yield. Therefore, it is used usually within a range of from 85 to 105 mol %, preferably from 97 to 103 mol %, of the stoichiometric amount.

As the catalyst, a molybdenum compound such as ammonium molybdate or molybdenum oxide is employed in the same manner as in the conventional methods. The catalyst is used in an amount of from 0.01 to 0.5% by weight relative to the phthalic acid starting material.

As the solvent to be used for the reaction of the present invention, it is preferred that the solvent itself has good thermal stability, it is not reactive with other reaction product during the reaction and it is liquid at room temperature. Further, it preferably has a boiling point at a level of from 180° to 250° C., and the boiling point range is preferably narrow. As such an organic solvent, an alkylbenzene, a halogenated aromatic compound, a nitroaromatic compound or a saturated aliphatic hydrocarbon may be mentioned. Specifically, nitrobenzene, trichlorobenzene, t-butylbenzene, t-amylbenzene, isopropylxylene, naphthalene, decalin, tetralin or a saturated aliphatic hydrocarbon having from 10 to 12 carbon atoms (n-undecane) may be mentioned.

The solvent is used usually in a amount of at least 250 to 300 ml relative to one mol of phthalic acid starting material. However, the fluidity of the reaction solution varies depending upon the type of the solvent for the reaction. For example, in the case of nitrobenzene, if cyanuric acid and/or a cyanuric acid derivative is not added, the fluidity of the reaction product during the reaction is fairly good as compared with the case of the alkylbenzene or trichlorobenzene as mentioned above. When cyanuric acid and/or its derivative is added, the fluidity will be further improved, and the reaction yield of copper phthalocyanine will be improved by about 1%. In the case where an alkylbenzene is used as the reaction solvent, if cyanuric acid and/or its derivative is not added, the fluidity of the reaction product becomes extremely poor during the reaction, particularly towards the end of the reaction, as mentioned above. Whereas, when cyanuric acid and/or its derivative is added at the initiation of the reaction or during the reaction, the fluidity will be remarkably improved particularly towards the end of the reaction, whereby the torque of the reaction product exerted to the stirring vanes decreases substantially, and its change with time will be substantially moderated as compared with the case where cyanuric acid and/or its derivative is not added. Not only that, it has been found surprisingly that the reaction yield is improved by about 3%.

The reaction product is subjected to distillation under reduced pressure to remove the solvent by a usual method, then washed with hot water and dried. Crude phthalocyanine thereby obtained (hereinafter referred to simply as a crude) has the purity improved by about 2% and the unreacted copper content (hereinafter referred to as free copper) reduced by about 50% as compared with the one prepared by the conventional method. Also in the case where trichlorobenzene is used as the solvent for the reaction, when cyanuric acid/or its derivative is added during the reaction, a reduction of the torque for stirring the reaction product during the reaction and an improvement of the reaction yield are likewise observed, but such effects are not so remarkably as in the case where an alkylbenzene is used as the solvent for the reaction.

The amount of cyanuric acid and/or its derivative to be added in the urea method of the present invention is preferbly from 2 to 30% by weight as calculated as cyanuric acid, relative to phthalic anhydride/or its derivative as the starting material. Namely, if the amount is less than 2% by weight, no improvement will be observed in both the fluidity of the reaction product during the reaction and the reaction yield. On the other hand, if the amount exceeds 30% by weight, the reaction yield tends to decrease although an improvement in the fluidity of the reaction product during the reaction is observed.

The effect for improvement of the reaction yield by the addition of cyanuric acid and/or its derivative, appears when the amount of addition reaches 2% by weight. At this stage, a reduction of the torque of the reaction product is not distinctly recognized, but the change with time of the torque starts to be different from the case where cyanuric acid/or its derivative is not added, when the amount of the addition reaches 2% by weight. It is when the amount of cyanuric acid and/or its derivative reaches 5% by weight that both effects for the improvement of the reaction yield and the decrease of the torque with time of the reaction product appear simultaneously.

With respect to the timing of the addition of cyanuric acid/or its derivative to the reaction starting material system, the predetermined amount may be added all at once or portionwise at the initiation of the reaction and/or during the reaction. However, if the above-mentioned at least 5% by weight of cyanuric acid and/or its derivative is added at the final stage of the reaction, particularly after the abrupt increase of the stirring torque of the reaction product, the abovementioned decrease of the torque of the reaction product or the improvement in the reaction yield can not be obtained, and no effects will be attained by the addition.

It has not yet been clearly understood why the stirring torque of the reaction product decreases and the reaction yield improves by the addition of cyanuric acid and/or its derivative (hereinafter referred to simply as a cyanuric acid) over the case where no such cyanuric acid is added, as described above. However, if the reaction for the synthesis of copper phthalocyanine is conducted by using a cyanuric acid only i.e. without using urea, copper phthalocyanine will be formed only in a trace amount. Yet, when the reaction for the synthesis for copper phthalocyanine is conducted in accordance with the present invention, the added cyanuric acid will remain in the reaction product after the completion of the reaction together with cyanuric acid formed by heat decomposition of urea during the reaction. Therefore, it is believed that as opposed to urea or biuret, it does not function as a nitrogen-supplier and does not serve as a starting material for reaction. Thus, a cyanuric acid is believed to be present as a non-reactant in the intermediate phthalocyanine product and/or among fine crystals of phthalocyanine formed by the reaction, to change the agglomeration condition of the fine crystals, thus bringing about a decrease of the torque of the reaction product, which in turn reduces partial heating of the reaction product and thus improves the reaction yield.

It is further advantageous that the cyanuric acid remaining in the reaction product as it is, has extremely small solubility in water at normal temperature although it is soluble in hot water. After distilling off the solvent under reduced pressure from the reaction product, the residue is washed with hot water to obtain crude copper phthalocyanine. When the hot water used for washing is cooled as it is or after concentration, it is possible to precipitate almost all the cyanuric acid, which can readily be recovered in high purity by filtration and drying. The recovered product can be reused by adding it to the reaction materials as it is. In addition, by evaporating the hot water used for washing to dryness and washing the dried residue with a small amount of cool water, it is possible to recover at least 95% of the cyanuric acid and an unreacted phthalic acid component contained in the hot water used for washing. The cyanuric acid containing the unreacted phthalic acid component thus obtained by the evaporation to dryness-washing with cool water method can also be reused by adding it to the starting materials for reaction.

Such excellent effects of the addition of cyanuric acid and/or its derivative to the reaction system are obtainable not only in the case of the reaction for the synthesis of copper phthalocyanine by the urea method but also in the cases of phthalocyanines of metals other than copper, such as iron, cobalt, nickel, manganese, aluminum, gallium, indium, chromium, zinc, magnesium and calcium prepared by the urea method.

It has been also found surprisingly that also in the case of the reaction for the synthesis of a metal phthalocyanine by a so-called phthalodinitrile method wherein phthalodinitrile is used as the starting material as is different from the above described urea method, it is possible to obtain a crude metal phthalocyanine having higher purity with higher performance than that obtainable by the above urea method in good yield, when the reaction for the synthesis is conducted by an addition of cyanuric acid/or its derivative to the reaction system in the same manner as in the urea method.

Now, the present invention will be described in further detail with reference to the Examples. However, it should be understood that the present invention is by no means restricted to such specific Examples. In the Examples, "parts" and "%" mean "parts by weight" and "% by weight", unless otherwise specified.

EXAMPLE 1

Into a four-necked pressure reactor made of glass having a capacity of 1,000 ml and equipped with an anchor type stirrer, a condenser and a thermometer, 180 parts of phthalimide, 169 parts of urea, 30.3 parts of cuprous chloride, 0.09 part of ammonium molybdate, 13.1 part of cyanuric acid and 324 parts of t-amylbenzene were charged and heated in an oil bath at a temperature of from 170° to 210° C. for 4.5 hours for reaction. The fluidity of the reaction product was good throughout the reaction.

After completion of the reaction, the reaction product was subjected to distillation under reduced pressure to remove the solvent, and the residue was subjected to washing with hot water and to filtration. The washing with water of the cake (cake shower) was conducted by using hot water in an amount of at least three times the amount of the cake. The cake obtained by the filtration was dried at 130° C. for 12 hours, to obtain 176 parts of crude copper phthalocyanine (hereinafter referred to simply as a crude). The purity of the crude was 97%, and the free copper contained in the crude was 0.30%. The yield of the crude was 97 mol %.

COMPARATIVE EXAMPLE 1

The reaction for the synthesis was conducted in the same manner as in Example 1 except that no cyanuric acid was added in Example 1. Upon expiration of about 2.5 hours from the initiation of the reaction, the torque exerted the stirring vanes remarkably increased, and the fluidity of the reaction product became so poor that its movement was very little.

As a result, 174 parts of a crude was obtained. The purity of the crude was 94%, the yield was 93 mol %, and the free copper contained therein was 0.75%.

Preparation of pigments

Then, the crudes obtained in Example 1 and Comparative Example 1 were, respectively, charged into kneaders together with diethylene glycol and sodium chloride, heated to an internal temperature of from 80° to 85° C. and formed into pigments by a wet pulverization method.

The respective pigments thus obtained were formed into inks, and the colors were measured in accordance with the method of JIS K-5101. As a result, the crude of Example 1 was found to be distinctly superior in the clearness to the conventional crude of Comparative Example 1 prepared without an addition of cyanuric acid.

EXAMPLE 2

The reactions were conducted in the same manner as in Example 1 except that the amount of cyanuric acid in Example 1 was changed to from 3.6 parts (2% by weight relative to phthalimide) to 63 parts (35% by weight relative to phthalimide) as identified in the following Table 1, to examine the effects of the amount of the addition of cyanuric acid over the reaction for the synthesis of copper phthalocyanine. The results are shown in Table 1 together with the results of Example 1 and Comparative Example 1.

TABLE 1

| Amount of cyanuric acid relative to phthalimide (wt %) | Crude copper phthalocyanine (Crude) | | | Example Nos. |
|---|---|---|---|---|
| | Yield relative to phthalimide (mol %) | Purity (wt %) | Free copper content (wt %) | |
| 0.0 | 93.0 | 94.0 | 0.75 | Comparative Example 1 |
| 2.0 | 94.0 | 94.5 | 0.65 | Example 2 |
| 5.0 | 95.0 | 95.0 | 0.60 | Example 2 |
| 7.3 | 97.0 | 97.0 | 0.30 | Example 1 |
| 13.2 | 97.1 | 97.0 | 0.31 | Example 2 |
| 25.0 | 94.0 | 94.5 | 0.67 | Example 2 |
| 35.0 | 91.0 | 92.0 | 1.22 | Example 2 |

EXAMPLE 3

The operation was conducted in the same manner as in Example 1 except that 13.1 parts of cyanuric acid used in Example 1 was changed to 15.3 parts of sodium cyanurate, whereby exactly the same results as in Example 1 were obtained.

EXAMPLE 4

The operation was conducted in the same manner as in Example 1 except that 13.1 parts of cyanuric acid used in Example 1 was changed to 17.0 parts of potassium cyanurate, whereby exactly the same results as in Example 1 were obtained.

EXAMPLE 5

Into the same reactor as used in Example 1, 180 parts of phthalimide, 294 parts of urea, 60.8 parts of ferrous chloride tetrahydrate, 0.9 part of ammonium molybdate, 20.0 parts of cyanuric acid and 324 parts of t-amylbenzene were charged and heated in an oil bath at a temperature of from 170° to 210° C. for 5 hours for reaction. The fluidity of the reaction product was good throughout the reaction.

The reaction product was subjected to distillation under reduced pressure to remove the solvent, and the residue was stirred and washed with a 5% sulfuric acid aqueous solution at a temperature of from 60° to 70° C. and subjected to filtration. Then, the cake obtained by filtration was subjected to cake shower thoroughly with hot water of from 60° to 70° C. until the cake was free from acid and then dried at 130° C. for at least 12 hours, to obtain 161.2 parts of crude iron phthalocyanine (hereinafter referred to simply as a crude). The purity of the crude was 97%, and the yield was 90 mol %.

COMPARATIVE EXAMPLE 2

The reaction for the synthesis was conducted in the same manner as in Example 5 except that no cyanuric acid was added in Example 5. Upon expiration of about two hours from the initiation of the reaction, the torque exerted to the stirring vanes remarkably increased, and the reaction product along the inner all of the reactor did not move or flow.

As a result, 146.3 parts of crude iron phthalocyanine (crude) was obtained. Purity of this crude was 95%, and the yield was 80 mol %.

EXAMPLE 6

Into the same reactor as used in Example 1, 180 parts of phthalimide, 330 parts of urea, 0.9 part of ammonium molybdate, 72.8 parts of cobalt chloride hexahydrate, 22.4 parts of cyanuric acid and 324 parts of t-amylbenzene were charged and heated in an oil bath at a temperature of from 170° to 210° C. for five hours for reaction. The fluidity of the reaction product was good during the reaction.

The reaction product was subjected to distillation under reduced pressure to remove the solvent, and the residue was stirred and washed with a 5% sulfuric acid aqueous solution at a temperature of from 60° to 70° C. and subjected to filtration. The cake obtained by the filtration was subjected to cake shower thoroughly with hot water of from 60° to 70° C. until the cake was free from acid and then dried at 130° C. for 12 hours, to obtain 167.6 parts of crude cobalt phthalocyanine (crude). The purity of the crude was 97%, and the yield was 93 mol %.

COMPARATIVE EXAMPLE 3

The reaction for the synthesis was conducted in the same manner as in Example 6 except that no cyanuric acid was added in Example 6. Upon expiration of about two hours from the initiation of the reaction, the torque exerted to the stirring vanes remarkably increased, and the reaction product along the inner wall of the reactor did not move or flow.

As a result, 153 parts of crude cobalt phthalocyanine (crude) was obtained. The purity of this crude was 96%, and the yield was 84 mol %.

EXAMPLE 7

Into the same reactor as used in Example 1, 22.0 parts of cuprous chloride, 120.0 parts of phthalodinitrile, 360 parts of α-chloronaphthalene and 20.0 part of cyanuric acid were charged and heated in an oil bath at a temperature of from 180° to 260° C. for 5 hours for reaction.

The fluidity of the reaction product was good throughout the reaction.

The reaction product was subjected to distillation under reduced pressure to remove the solvent, and the residue was stirred and washed with a 5% sulfuric acid aqueous solution at a temperature of from 60° to 70° C. and subjected to filtration. Then, the cake obtained by the filtration was washed with hot water of from 60° to 70° C. until the filtrate was free from acid. Then, the cake was dried at a temperature of 130° C. for 12 hours, to obtain 114 parts of crude copper phthalocyanine (crude). The purity of the crude was 98.0%, and the yield was 83 mol %.

COMPARATIVE EXAMPLE 4

The reaction for the synthesis was conducted in the same manner as in Example 7 except that no cyanuric acid was added in Example 7. Upon expiration of about two hours from the initiation of the reaction, the torque exerted to the stirring vanes remarkably increased, and the fluidity of the reaction product was extremely poor so that the reaction product along the inner wall of the rector did not move even though the stirring vanes moved.

As a result, crude phthalocyanine (crude) was obtained only in an amount of 93 parts. The purity of the crude was 97%, but the yield was 67 mol %.

As is evident from the above results, the process for producting metal phthalocyanines according to the present invention is not only industrially advantageous in that the serious problems of the conventional processes such as a decrease of the fluidity of the reaction product during the reaction and a decrease in the reaction yield due to dilution with a solvent can be completely solved in either the so-called urea method or the phthalodinitrile method by a novel method of adding cyanuric acid and/or its derivative to the reaction starting material system, but also provides industrially valuable remarkable effects that crude metal phthalocyanines having higher purity and higher performance than ever are obtainable in good yield, and cyanuric acid and/or its derivative used can readily and completely be recovered and reused.

What is claimed is:

1. In a process for producing a metal phthalocyanine compound by heating phthalic acid and/or its derivative selected from the group consisting of the anhydride, the ammonium salt, the imide, the ester, the amide thereof and orthocyanobenzoic acid, urea and a metal compound wherein the metal is selected from the group consisting of copper, cobalt, nickel, manganese, indium, potassium, calcium or magnesium, in an organic solvent in the presence of a catalyst, or by heating phthalodinitrile and said metal in an organic solvent, the improvement wherein the fluidity of the reaction process is improved by the addition of from 2 to 30% by weight, relative to phthalic acid or its derivative or relative to phthalodinitrile, of cyanuric acid and/or the alkali metal salts thereof.

2. The process according to claim 1, wherein the alkali metal is sodium.

3. The process according to claim 1, wherein the alkali metal is the potassium.

* * * * *